United States Patent
D'Angio et al.

(10) Patent No.: US 7,230,012 B2
(45) Date of Patent: Jun. 12, 2007

(54) PHARMACEUTICAL COMPOSITIONS AND DOSAGE FORMS OF THALIDOMIDE

(75) Inventors: Paul D'Angio, Basking Ridge, NJ (US); John McCarty, Miami Springs, FL (US)

(73) Assignee: Celgene Corporation, Summit, NJ (US)

( * ) Notice: Subject to any disclaimer, the term of this patent is extended or adjusted under 35 U.S.C. 154(b) by 162 days.

(21) Appl. No.: 10/608,077

(22) Filed: Jun. 30, 2003

(65) Prior Publication Data

US 2004/0138263 A1 Jul. 15, 2004

Related U.S. Application Data

(60) Provisional application No. 60/426,016, filed on Nov. 14, 2002.

(51) Int. Cl.
*A61K 31/445* (2006.01)
*A61K 9/48* (2006.01)

(52) U.S. Cl. .................... 514/323; 514/323; 424/451

(58) Field of Classification Search .................... None
See application file for complete search history.

(56) References Cited

U.S. PATENT DOCUMENTS

| | | | | |
|---|---|---|---|---|
| 5,385,901 A | | 1/1995 | Kaplan et al. ............ | 514/231.5 |
| 5,405,855 A | | 4/1995 | Andrulis, Jr. et al. ....... | 514/323 |
| 5,434,170 A | | 7/1995 | Andrulis, Jr. et al. ....... | 514/323 |
| 5,593,990 A | | 1/1997 | D'Amato ................. | 514/235.2 |
| 5,629,327 A | | 5/1997 | D'Amato ................. | 514/323 |
| 5,643,915 A | * | 7/1997 | Andrulis et al. ............ | 514/279 |
| 5,654,312 A | | 8/1997 | Andrulis, Jr. et al. ....... | 514/279 |
| 5,712,291 A | | 1/1998 | D'Amato ................. | 514/323 |
| 5,731,325 A | | 3/1998 | Andrulis, Jr. et al. ....... | 514/323 |
| 6,001,828 A | | 12/1999 | Andrulis, Jr. et al. ....... | 514/221 |
| 6,071,948 A | | 6/2000 | D'Amato ................. | 514/416 |
| 6,114,355 A | | 9/2000 | D'Amato ................. | 514/323 |
| 6,140,346 A | | 10/2000 | Andrulis, Jr. et al. ....... | 514/323 |
| 6,228,879 B1 | | 5/2001 | Green et al. .............. | 514/416 |
| 6,235,756 B1 | | 5/2001 | D'Amato ................. | 514/323 |
| 6,469,045 B1 | | 10/2002 | D'Amato ................. | 514/416 |
| 6,914,067 B2 | * | 7/2005 | Govindarajan et al. ..... | 514/283 |
| 2003/0191098 A1 | | 10/2003 | D'Amato ................. | 514/171 |

OTHER PUBLICATIONS

Baker et al., Efficacy of Thalidomide in the Treatment of Relapsed and Refractory Myeloma, Haematology Society of Australia and New Zealand, Abstracts Jul. 25-28, 2000, 54.*

Gennaro, Remington: The Science and Practice of Pharmacy, Mack Publishing Co. 19th, 1618, 1642-1644.*
Scheffler et. al., 1999, Clin Pharmacol Ther, 65, 483-490.*
Teo et. al, 1999, Journal of Clinical Pharmacology, 39, 1162-1168.*
Teo et al., 2000, Biopharmaceutics and Drug Disposition, 21, 33-40.*
"Thalomid," *Physician's Desk Reference*, 53th Ed., pp. 3457-3462 (1999).
"Thalomid," *Physician's Desk Reference*, 54th Ed., pp. 911-916 (2000).
"Thalomid," *Physician's Desk Reference*, 55th Ed., pp. 1081-1085 (2001).
"Thalomid," *Physician's Desk Reference*, 56th Ed., pp. 1154-1158 (2002).
"Thalomid," *Physician's Desk Reference*, 57th Ed., pp. 1153-1157 (2003).
"Thalomid," *Physician's Desk Reference*, 58th Ed., pp. 1122-1127 (2004).
"Thalomid," *Physician's Desk Reference*, 59th Ed., pp. 1095-1099 (2005).
"Thaildomide," Printout from www.grunenthal.com/cw/en_EN/html/cw_en_en_aboutus.jhtml?CatId=cw_en_en_aboutus_e_01 (date unknown).
"Getting Thalidomide," Printout from http://www.4imago.com/mpd/mexico.htm (May 12, 2004).
"Talizer," Printout from http://216.239.37.104/translate_c?hl=en&sl=es&u=http://wwww.facmed.unam.mx/bmnd/pl (date unknown).
"Sauramide," Printout from http://www.kodc.or.kr/jaga/suaramide_photo.htm (date unknown).
"Notice Destinee Au Patient," Notice to Patients regarding Thalidomide Laphal (Date unknown).
"Historical Timeline," Printout from http://www.pharmion.com/corporateweb/home.nsf/Content/Historical Timeline (date unknown).
"Thalidomide 100 mg Tablets (EntreMed Formulation)," Celgene internal document (date unknown).
"Products," Printout from http://www.daburpharma.com/htmls/prod_form.html (date unknown).

(Continued)

*Primary Examiner*—Frederick Krass
*Assistant Examiner*—Lezah Roberts
(74) *Attorney, Agent, or Firm*—Jones Day

(57) ABSTRACT

Pharmaceutical compositions and single unit dosage forms of thalidomide and pharmaceutically acceptable prodrugs, salts, solvates, hydrates, or clathrates are disclosed. Also disclosed are methods of treating and preventing diseases and conditions such as, but not limited to, leprosy, chronic graft-vs-host disease, rheumatoid arthritis, sarcoidosis, an inflammatory condition, inflammatory bowel disease, and cancer using the novel dosage forms disclosed herein.

10 Claims, No Drawings

OTHER PUBLICATIONS

"Myrin (Thaidomide)," Printout from http://www.lipomed.com/Pharma/myrin/overview/ (date unknown).
"Thalidomide," The Merck Index, 11th Ed., p. 9182 (1989).
"Thalidomide," The Merck Index, 12th Ed., p. 9389 (1996).
"Thalidomide," The Merck Index, 13th Ed., p. 9323 (2001).
Guo et al., "A prototype intelligent hybrid system for hard gelatin capsule formulation development," *Pharmaceutical Technology*, pp. 44-60 (Sep. 2002).
Rouhi, "Thalidomide," Chemical & Engineering News, pp. 122-123 (Jun. 20, 2005).
"Thalidomide," *Drugs of the Future*, Entry # 91361 (2005).
Abdel-Razeq et al., *Drugs of the Future*, 29(10): 1059-1063(2004).
Sommer, *Drugs of the Future*, 24(1):67-75 (1999).
"Thalidomide," *Drug Data Report*, 17(5):468 (1995).
"Thalidomide," *Drug Data Report*, 17(5):482 (1995).
"Thalidomide," *Drug Data Report*, 20(11):962 (1998).

* cited by examiner

PHARMACEUTICAL COMPOSITIONS AND DOSAGE FORMS OF THALIDOMIDE

This application claims priority to provisional application No. 60/426,016, filed Nov. 14, 2002, the entirety of which is incorporated herein by reference.

1. FIELD OF THE INVENTION

The present invention relates, in part, to pharmaceutical compositions and dosage forms comprising thalidomide and pharmaceutically acceptable prodrugs, salts, solvates, hydrates, and clathrates thereof.

2. BACKGROUND OF THE INVENTION

Thalidomide is a racemic compound sold under the tradename THALOMID® and chemically named α-(N-phthalimido)glutarimide or 2-(2,6-dioxo-3-piperidinyl)-1H-isoindole-1,3(2H)-dione. Thalidomide was originally developed to treat morning sickness, but due to tetragenic effects it was withdrawn from use. Thalidomide is currently approved in the United States for the treatment of erythema nodosum leprosum in humans. *Physician's Desk Reference®*, 1081-1085 (55th ed., 2001).

Thalidomide has reportedly been used on patients with leprosy, chronic graft-vs-host disease, rheumatoid arthritis, sarcoidosis, several inflammatory skin diseases, and inflammatory bowel disease. See generally, Koch, H. P., 22 *Prog. Med. Chem.* 165-242 (1985). See also, Moller, D. R., et al., 159 *J. Immunol.* 5157-5161 (1997); Vasiliauskas, E. A., et al., 117 *Gastroenterology* 1278-1287 (1999); and Ehrenpreis, E. D., et al., 117 *Gastroenterology* 1271-1277 (1999). It has further been alleged that thalidomide can be combined with other drugs to treat iscehemia/reperfusion associated with coronary and cerebral occlusion. U.S. Pat. No. 5,643,915.

More recently, thalidomide has been used in the treatment of specific types of cancers. These include refractory multiple myeloma, brain, melanoma, breast, colon, mesothelioma, and renal cell carcinoma. See, e.g., Singhal, S., et al., 341(21) *New England J. Med.*, 1565-1571 (1999); and Marx, G. M., et al., 18 *Proc. Am. Soc. Clin. Oncology*, 454a (1999). It has further been reported that thalidomide has been used to prevent the development of chronic cardiomyopathy in rats caused by doxorubicin. Costa, P. T., et al., 92(10:suppl. 1) *Blood*, 235b (1998). Other reports concerning the use of thalidomide in the treatment of specific cancers include combination with carboplatin in the treatment of glioblastoma multiforme. McCann, J., *Drug Topics* 41-42 (Jun. 21, 1999). Thalidomide has reportedly also been used as an antiemetic during the treatment of astrocytoma. Zwart, D., 16(12) *Arzneim.-Forsch.*, 1688-1689 (1966). A method of inhibiting of angiogenesis is disclosed by U.S. Pat. No. 6,235,756 B1, which is incorporated herein by reference.

Thalidomide is administered to patients orally. Presently, thalidomide is orally administered in a size #0 capsule shell containing 12.5 percent weight by total weight of the composition. The capsule fill weight is 400 mg, so only 50 mg of thalidomide are included per capsule. For use in the treatment of diseases such as cancer, however, 200 mg to 800 mg dosages are commonly required. Therefore, patients may have to ingest 4 to 16 capsules of thalidomide to receive a therapeutically effective amount of the drug. Because of the large size of the #0 capsule and the large amount of thalidomide required to treat certain diseases and conditions, patient compliance may be problematic. To be specific, some patients may not take thalidomide in its currently available oral dosage form as often or in the large amounts necessary to effectively treat their disease. Therefore, a need exists for new pharmaceutical dosage forms of thalidomide.

3. SUMMARY OF THE INVENTION

This invention encompasses novel pharmaceutical dosage forms of thalidomide and pharmaceutically acceptable prodrugs, salts, solvates, hydrates, and clathrates thereof. The invention further encompasses methods of treating or preventing diseases and conditions such as, but not limited to, leprosy, chronic graft-vs-host disease, rheumatoid arthritis, sarcoidosis, an inflammatory condition, inflammatory bowel disease, and cancer, using thalidomide and pharmaceutically acceptable prodrugs, salts, solvates, hydrates, and clathrates thereof in the novel dosage forms described herein.

3.1. Definitions

As used herein and unless otherwise indicated, a composition that is "substantially free" of a compound means that the composition contains less than about 20 percent by weight, more preferably less than about 10 percent by weight, even more preferably less than about 5 percent by weight, and most preferably less than about 3 percent by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80 percent by weight of one stereoisomer of the compound and less than about 20 percent by weight of other stereoisomers of the compound, more preferably greater than about 90 percent by weight of one stereoisomer of the compound and less than about 10 percent by weight of the other stereoisomers of the compound, even more preferably greater than about 95 percent by weight of one stereoisomer of the compound and less than about 5 percent by weight of the other stereoisomers of the compound, and most preferably greater than about 97 percent by weight of one stereoisomer of the compound and less than about 3 percent by weight of the other stereoisomers of the compound.

As used herein and unless otherwise indicated, the term "enantiomerically pure" means a stereomerically pure composition of a compound having one chiral center.

As used herein, unless otherwise specified, the term "pharmaceutically acceptable salt(s)," as used herein includes, but is not limited to, salts of acidic or basic moieties of thalidomide. Basic moieties are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (i.e., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein to describe a compound or chemical moiety, the term "derivative" means a compound or chemical moiety wherein the degree of saturation of at least one bond has been changed (e.g., a single bond has been changed to a double or triple bond) or wherein at least one hydrogen atom is replaced with a different atom or a chemical moiety. Examples of different atoms and chemical moieties include, but are not limited to, halogen, oxygen, nitrogen, sulfur, hydroxy, methoxy, alkyl, amine, amide, ketone, and aldehyde.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of thalidomide that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of thalidomide that include —NO, —NO$_2$, —ONO, or —ONO$_2$ moieties.

As used herein and unless otherwise indicated, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

4. DETAILED DESCRIPTION OF THE INVENTION

This invention encompasses novel pharmaceutical dosage forms of thalidomide and pharmaceutically acceptable prodrugs, salts, solvates, hydrates, and clathrates thereof. Preferred dosage forms are suitable for oral administration to a patient. Preferred oral dosage forms of thalidomide comprise a higher weight percent of thalidomide than prior oral dosage forms of the drug. Preferred oral dosage forms of thalidomide are either bioequivalent to the oral dosage forms of the drug currently approved by the Food and Drug Administration in the United States, or provide better bioavailability than currently approved dosage forms.

The invention also encompasses kits comprising pharmaceutical compositions and dosage forms of the invention. Also encompassed by the invention are methods of treating and preventing diseases and conditions which include administering to patients in need thereof pharmaceutical compositions and dosage forms of the invention.

For example, this invention encompasses a single unit dosage form suitable for oral administration to a human comprising: greater than about 1, 5, 10, 15, 20, 25 mg, or 30 mg of an active ingredient; and an excipient; wherein the active ingredient is thalidomide or a pharmaceutically acceptable produg, salt, solvate, or clathrate thereof. Preferably, the amount of active ingredient is from about 5 to about 10 weight percent when the active ingredient is about 1 to about 5 mgs.

A particular embodiment of the invention encompasses a single unit dosage form suitable for oral administration to a human comprising: greater than about 25 mg of an active ingredient; and an excipient; wherein the active ingredient is thalidomide or a pharmaceutically acceptable produg, salt, solvate, or clathrate thereof. Preferably, the amount of active ingredient is from about 30 to about 50 weight percent, more preferably about 40 weight percent when the active ingredient is about 25 mgs or more.

A specific example of this embodiment is a single unit dosage form suitable for oral administration to a human comprising: about 50 mg of an active ingredient, wherein the active ingredient is thalidomide or a pharmaceutically acceptable prodrug, salt, solvate, or clathrate thereof; about 74 mg of a carrier, diluent or filler, wherein the carrier, diluent or filler comprises pregelatinized corn starch or microcrystalline cellulose or silicified microcrystalline cellulose or dicalcium phosphate; and about 1 mg of magnesium stearate; wherein the single unit dosage form is a capsule of size #4.

Another specific example encompasses a single unit dosage form suitable for oral administration to a human comprising: about 40 weight percent of an active ingredient, wherein the active ingredient is thalidomide or a pharmaceutically acceptable produg, salt, solvate, or clathrate thereof; about 53 weight percent of a binder, wherein the binder comprises pregelatinized corn starch or microcrystalline cellulose; about 4 weight percent surfactant; about 2 weight percent disintegrant; and about 1 weight percent lubricant; wherein the single unit dosage form is a tablet.

Another embodiment of the invention encompasses a method for treating or preventing leprosy, chronic graft-vs-host disease, rheumatoid arthritis, sarcoidosis, an inflammatory condition, inflammatory bowel disease, or cancer, which comprises administering to a patient in need of such treatment or prevention a single unit dosage form of the invention. In a preferred method, the disease is cancer.

This invention encompasses pharmaceutical compositions and single unit dosage forms of racemic and stereomerically pure thalidomide, and pharmaceutically acceptable prodrugs, salts, solvates, hydrates, and clathrates thereof.

Thalidomide is commercially available, but can also be prepared by methods known in the art. See, e.g., *The Merck Index*, p. 9182 (11th ed.; 1989), and the references disclosed therein.

4.1. Pharmaceutical Compositions and Dosage Forms

Pharmaceutical compositions and dosage forms of the invention contain a prophylactically or therapeutically effective amount of an active ingredient (i.e., thalidomide or a pharmaceutically acceptable prodrug, salt, solvate, hydrate, or clathrate thereof) and an excipient. Preferred dosage forms are suitable for oral administration, and can be coated to reduce or avoid degradation of the active ingredient within the gastrointestinal tract.

Pharmaceutical compositions and dosage forms of the invention may also contain one or more secondary active ingredients. Examples of secondary active ingredients include, but are not limited to, anti-cancer drugs. Examples of anti-cancer drugs include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Preferred pharmaceutical compositions and dosage forms contain greater than about 25 weight percent active ingredient (i.e., thalidomide or a pharmaceutically acceptable prodrug, salt, solvate, hydrate, or clathrate thereof). Pharmaceutical compositions and dosage forms are encompassed by the invention that contain the active ingredient in an amount of from about 30 percent to about 50 percent by weight, preferably from about 35 percent to about 45 percent by weight, and most preferably about 40 percent by weight of the total composition or dosage form.

Pharmaceutical compositions and dosage forms of the invention preferably contain one or more excipients in an amount of less than about 75 percent by weight of the total composition or dosage form. Pharmaceutical compositions and dosage forms are encompassed by the invention that contain the excipient(s) in an amount of from about 50 percent to about 70 percent by weight, preferably from about 55 percent to about 65 percent by weight, more preferably in an amount of about 60 percent by weight.

Excipients include carriers, diluents, fillers, lubricants and glidants. One embodiment of the invention encompasses a pharmaceutical composition that includes thalidomide, and a carrier, diluent or filler. The carrier, diluent or filler is preferably present in an amount from about 50 percent to about 75 percent by weight, preferably from about 55 percent to about 65 percent by weight. A preferred pharmaceutical composition further includes a lubricant or glidant in an amount of from about 0.01 percent to about 4 percent by weight, and more preferably in an amount from about 0.1 percent to about 1 percent. In yet another embodiment, the composition further includes a disintegrant, preferably in an amount from about 1 percent to about 8 weight percent, more preferably from about 1 percent to about 3 weight percent.

Carriers, diluents and fillers suitable for use in pharmaceutical compositions and dosage forms include, but are not limited to, calcium carbonate, calcium phosphate, dibasic calcium phosphate, tribasic calcium sulfate, calcium carboxymethylcellulose, cellulose, cellulose (e.g., microcrystalline cellulose, silicified microcrystalline cellulose, and cellulose acetate), dextrates, dextrin, dextrose (glucose), fructose, lactitol, lactose, magnesium carbonate, magnesium oxide, matitol, maltodextrins, maltose, sorbitol, starch (e.g., pregelatinized starch), sucrose, sugar, and xylitol.

One example of a pre-gelatinized starch is SPRESS B-820. Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), PROSOLV SMCC 90HD (Penwest, Patterson, N.Y.), and mixtures thereof. Carriers, diluents and fillers may also be used in premixes.

Lubricants that can be used in pharmaceutical compositions and dosage forms of the invention include, but are not limited to, agar, calcium stearate, ethyl oleate, ethyl laureate, glycerin, glyceryl palmitostearate, hydrogenated vegetable oil (e.g., corn oil, cottonseed oil, olive oil, peanut oil, sesame oil, soybean oil, and sunflower oil), magnesium oxide, magnesium stearate, mannitol, poloxamer, glycols (e.g., polyethylene glycol), sodium benzoate, sodium lauryl sulfate, sodium stearyl, sorbitol, stearic acid, talc, zinc stearate, and mixtures thereof.

Glidants include, for example, coagulated aerosols of synthetic silica colliodal silicon dioxide, magnesium trisilicate, powdered cellulose, pyrogenic silicon dioxide products (e.g., CAB-O-SIL sold by Cabot Co. of Boston, Mass.), starch, syloid silica gels (e.g., AEROSIL 200, manufactured by W.R. Grace Co. of Baltimore, Md.), talc, tribasic calcium phosphate, and mixtures thereof. If used, lubricants are typically used in an amount of less than about 1 weight percent of the pharmaceutical compositions or dosage forms into which they are incorporated.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form the compositions of the invention. The amount of disintegrant used varies based upon the type of formulation, and is readily discernible to those of ordinary skill in the art. Disintegrants that can be used in pharmaceutical compositions and dosage forms of the invention include, but are not limited to, agar-agar, algins (e.g., alginic acid), calcium carbonate, carboxmethylcellulose, cellulose (e.g., hydroxypropyl cellulose, microcrystalline cellulose, and silicified microcrystalline cellulose), clays, colloid silicon dioxide, croscarmellose sodium, crospovidone, gums, magnesuim aluminium silicate, methylcellulose, polacrilin potassium, sodium alginate, sodium starch glycolate, starch (e.g., pregelatinized starch, potato starch, and tapioca starch), and mixtures thereof.

Pharmaceutical compositions and dosage forms can also contain wetting, emulsifying, and pH buffering agents.

Pharmaceutical compositions of the invention suitable for administration can be presented as discrete dosage forms, such as capsules (e.g., gelcaps), caplets, tablets, troches, lozenges, dispersions, and suppositories each containing a predetermined amount of an active ingredient as a powder or in granules, a solution, or a suspension in an aqueous or non-aqueous liquid, an oil-in-water emulsion, or a water-in-oil liquid emulsion. Because of their ease of administration, tablets, caplets, and capsules represent a preferred oral dosage unit forms.

Preferred tablets, caplets, and capsules contain from about 50 mg to about 500 mg of the pharmaceutical composition (i.e., active ingredient and excipient(s)), more preferably from about 125 mg to about 500 mg of the composition. Specific single unit dosage forms of the invention contain 50, 100, 150, 200, 250, 300, 350, 400, 450, 500, 750, or 1000 mg of active ingredient. Capsules can be of any size. Examples of standard sizes include #000, #00, #0, #1, #2, #3, #4, and #5. See, e.g., Remington's Pharmaceutical Sciences, page 1658-1659 (Alfonso Gennaro ed., Mack Publishing Company, Easton Pa., 18th ed., 1990). Preferred capsules of the invention are of size #0, #2, or #4.

A specific embodiment of the invention encompasses a single unit dosage form weighing about 125 mg, of which about 50 mg is active ingredient. In this embodiment, the composition is preferably loaded into a size #4 capsule. Another embodiment weighs about 250 mg, of which about 100 mg is active ingredient. In this embodiment, the composition is preferably loaded into a size #2 capsule. Yet another single unit dosage form weighs about 500 mg and contains about 200 mg active ingredient. In this embodiment, the composition is preferably loaded into a size #0 capsule.

Table 1 illustrates examples of oral dosage forms of thalidomide encompassed by the present invention:

TABLE 1

| Encapsulated thalidomide dosages | | |
| --- | --- | --- |
| Capsule Size | Capsule Weight (mg) | Thalidomide dose (mg) |
| #0 | 500 | 200 |
| #2 | 250 | 100 |
| #4 | 125 | 50 |

Also encompassed by this invention are anhydrous pharmaceutical compositions and dosage forms including an active ingredient, since water can facilitate the degradation of some compounds. For example, the addition of water (e.g., 5 percent) is widely accepted in the pharmaceutical arts as a means of simulating shelf-life, i.e., long-term storage in order to determine characteristics such as shelf-life or the stability of formulations over time. See, e.g., Jens T. Carstensen, *Drug Stability: Principles & Practice,* 2d. Ed., Marcel Dekker, N.Y., N.Y., 1995, pp. 379-80. In effect, water and heat accelerate decomposition. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that the anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastic or the like, unit dose containers, blister packs, and strip packs.

In this regard, the invention encompasses a method of preparing a solid pharmaceutical formulation including an active ingredient through admixing the active ingredient and an excipient under anhydrous or low moisture/humidity conditions, wherein the ingredients are substantially free of water. The method can further include packaging the anhydrous or non-hygroscopic solid formulation under low moisture conditions. By using such conditions, the risk of contact with water is reduced and the degradation of the active ingredient can be prevented or substantially reduced.

This invention further encompasses lactose-free pharmaceutical compositions and dosage forms. Compositions and dosage forms that comprise an active ingredient that is a primary or secondary amine are preferably lactose-free. As used herein, the term "lactose-free" means that the amount of lactose present, if any, is insuffficient to substantially increase the degradation rate of an active ingredient that is a primary or secondary amine.

Lactose-free compositions of the invention can comprise excipients which are well known in the art and are listed in the USP (XXI)/NF (XVI), which is incorporated herein by reference. In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

4.2. Process for Making Dosage Forms

Dosage forms of the present invention can be prepared by any of the methods of pharmacy, but all methods include the step of bringing the active ingredient into association with the excipient, which constitutes one or more necessary ingredients. In general, the compositions are prepared by uniformly admixing the active ingredient with liquid excipients or finely divided solid excipients or both, and then, if necessary, shaping the product into the desired presentation. If desired, tablets can be coated by standard aqueous or nonaqueous techniques.

A tablet or caplet of the invention can be prepared by compression or molding, optionally with one or more accessory ingredients. Compressed tablets can be prepared by compressing in a suitable machine the active ingredient in a free-flowing form such as powder or granules, optionally mixed with an excipient as above and/or a surface active or dispersing agent. Molded tablets can be made by molding in a suitable machine a mixture of the powdered compound moistened with an inert liquid diluent. Encapsulation of the dosage forms of the invention can be done using capsules of methylcellulose, calcium alginate, or gelatin.

4.2.1. Screening

The process for making the pharmaceutical compositions of the invention preferably includes the screening of the active ingredient and the excipient(s). Preferably, the active ingredient is passed through a screen having openings of about 430 microns to about 750 microns. More preferably, the active ingredient is passed through a screen with openings of about 600 microns to about 720 microns. In one embodiment, thalidomide is passed through a screen having openings of about 710 microns. Depending on the excipient(s) used, the screen openings vary. For example, disintegrants and binders are preferably passed through openings of about 430 microns to about 750 microns, more preferably from about 600 microns to about 720 microns, and most preferably about 710 microns. Lubricants are preferably passed through smaller openings, e.g., about 150 microns to about 250 microns screen. In one embodiment, the lubricant is passed through a screen opening of about 210 microns.

4.2.2. Pre-Blending

After the ingredients are screened, the excipient and active ingredient are preferably mixed in a diffusion mixer. In one embodiment, the mixing time is from about 1 minute to about 50 minutes, preferably from about 5 minutes to about 45 minutes. More preferably, the mixing time is from about 10 minutes to about 40 minutes, and most preferably the mixing time is from about 10 minutes to about 25 minutes. In another embodiment, the mixing time is about 15 minutes.

When more than one excipient is used, the excipients may be admixed in a tumble blender for about 1 minute to about 20 minutes, preferably for about 5 minutes to about 10 minutes, prior to mixing with the active ingredient.

4.2.3. Roller Compaction

In one embodiment, the pre-blend may be passed through a roller compactor with a hammer mill attached at the discharge of the compactor.

4.2.4. Final Blend

When a lubricant is used, e.g., magnesium stearate, the lubricant is mixed with the pre-blend at the end of the process to complete the pharmaceutical composition. This additional mixing is preferably from about 1 minute to about 10 minutes, more preferably about 3 minutes to about 5 minutes.

4.2.5. Encapsulation

The formulation mixture is then encapsulated into the desired size capsule shell using, for example, a capsule filling machine or a rotary tablet press.

4.3. Kits

Pharmaceutical packs or kits which comprise pharmaceutical compositions or dosage forms disclosed herein are also encompassed by the present invention. An example of a kit comprises notice in the form prescribed by a governmental agency regulating the manufacture, use or sale of pharmaceuticals or biological products, which notice reflects approval by the agency of manufacture, use or sale for human administration.

4.4. Methods of Treatment and Prevention

The present invention is also directed to methods of treating and preventing a wide variety diseases and conditions in patients (e.g., mammals, including humans). Examples of such disease and conditions include, but are not limited to, leprosy, chronic graft-vs-host disease, rheumatoid arthritis, sarcoidosis, inflammatory conditions (e.g., inflammation of the skin), inflammatory bowel disease, and cancer. Examples of cancers that can be treated using pharmaceutical compositions and dosage forms of the invention include, but are not limited to, primary and metastatic cancer of the head, neck, eye, mouth, throat, subcutaneous tissue, lymph nodes, esophagus, chest, bone, intestine, lung, colon, rectum, stomach, heart, prostate, breast, ovaries, adrenals, kidney, liver, pancreas, and brain. Specific examples of cancers that can be treated include, but are not limited to: AIDS associated leukemia and adult T-cell leukemia lymphoma; anal carcinoma; astrocytoma; biliary tract cancer; cancer of the bladder, including bladder carcinoma; brain cancer, including glioblastomas and medulloblastomas; breast cancer, including breast carcinoma; cervical cancer; choriocarcinoma; colon cancer including colorectal carcinoma; endometrial cancer; esophageal cancer; Ewing's sarcoma; gastric cancer; gestational trophoblastic carcinoma; glioma; hairy cell leukemia; head and neck carcinoma; hematological neoplasms, including acute and chronic lymphocytic and myelogeneous leukemia; hepatocellular carcinoma; Kaposi's sarcoma; kidney cancer; multiple myeloma; intraepithelial neoplasms, including Bowen's disease and Paget's disease; liver cancer; lung cancer including small cell carcinoma; lymphomas, including Hodgkin's disease, lymphocytic lymphomas, non-Hodgkin's lymphoma, Burkitt's lymphoma, diffuse large cell lymphoma, follicular mixed lymphoma, and lymphoblastic lymphoma; lymphocytic leukemia; neuroblastomas; oral cancer, including squamous cell carcinoma; ovarian cancer, including those arising from epithelial cells, stromal cells, germ cells and mesenchymal cells; pancreatic cancer; prostate cancer; rectal cancer; sarcomas, including soft tissue sarcomas, leiomyosarcoma, rhabdomyosarcoma, liposcarcoma, fibrosarcoma, and osteosarcoma; skin cancer, including melanoma, Kaposi's sarcoma, basal cell cancer and squamous cell cancer; testicular cancer, including testicular carcinoma and germinal tumors (e.g., semicoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilm's tumor. The term "colorectal carcinoma" refers to disease of skin tissues, organs, bloods, and vessels, of the colon, sigmoid, and/or rectum and within the vicinity of the colon, sigmoid, and/or rectum.

Other diseases and conditions that can be treated using pharmaceutical compositions of this invention are disclosed in U.S. Pat. Nos. 5,712,291 and 6,235,756 to D'Amato, both of which are incorporated herein by reference.

The invention also encompasses a method of reducing or preventing an adverse effect associated with chemotherapy or radiation therapy, which comprises administering to a patient in need of such treatment or prevention a pharmaceutical composition or dosage form of the invention in an amount sufficient to reduce an adverse effect associated with the chemotherapy or radiation therapy. This embodiment includes the use of pharmaceutical compositions and dosage forms to protect against or treat an adverse effect associated with the use of chemotherapy or radiation therapy, including raising a patient's tolerance for chemotherapy or radiation therapy.

Examples of adverse effects associated with chemotherapy and radiation therapy include, but are not limited to: gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure.

The actual amount of an active ingredient administered to a patient can depend on a variety of factors, such as, but not limited to, the disease or condition being treated or prevented, the specific active ingredient, and the method of its administration. For example, the dose and/or dose frequency may also vary according to age, body weight, response, and the past medical history of the patient. Suitable dosing regimens can be readily selected by those skilled in the art with due consideration of such factors by following, for example, dosages reported in the literature and recommended in the *Physician's Desk Reference®* (55th ed., 2001).

In one embodiment of the invention, an active ingredient is administered orally and daily in an amount of from about 50 to about 2000 mg, preferably from about 50 to about 1000 mg, and more preferably from about 50 to 800 mg. In a preferred embodiment, the recommended dose of active ingredient is from about 200 mg to about 800 mg.

5. EXAMPLES

Embodiments of the present invention may be more fully understood by reference to the following examples. While these examples are meant to be illustrative of pharmaceutical compositions and dosage forms made according to the present invention, the present invention is not meant to be limited by the following examples. All parts are by weight unless otherwise specified.

5.1. Example 1

200 mg Thalidomide Dosage Capsule

Table 2 illustrates a batch formulation and single dosage formulation for a 200 mg thalidomide single dose unit, i.e., about 40 percent by weight, in a size #0 capsule.

TABLE 2

| Formulation for 200 mg thalidomide capsule | | | |
|---|---|---|---|
| Material | Percent By Weight | Quantity (mg/tablet) | Quantity (kg/batch) |
| Thalidomide | 40.0% | 200 mg | 16.80 kg |
| Pregelatinized Corn Starch, NF | 59.5% | 297.5 mg | 24.99 kg |
| Magnesium Stearate | 0.5% | 2.5 mg | 0.21 kg |
| Total | 100.0% | 500 mg | 42.00 kg |

The pregelatinized corn starch (SPRESS B-820) and thalidomide components were passed through a 710 μm screen and then loaded into a Diffusion Mixer with a baffle insert and blended for 15 minutes. The magnesium stearate was passed through a 210 μm screen and added to the Diffusion Mixer. The blend was then encapsulated in a size #0 capsule, 500 mg per capsule (8400 capulse batch size) using a Dosator type capsule filling machine.

5.2. Example 2

100 mg Thalidomide Dosage Tablet

Table 3 illustrates a batch formulation and a single dose unit formulation for a 100 mg, i.e., 40 percent by weight, thalidomide single dose unit tablet.

TABLE 3

| Formulation for 100 mg thalidomide tablet | | | |
|---|---|---|---|
| Material | Percent by Weight | Quantity (mg/tablet) | Quantity (kg/batch) |
| Thalidomide | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and thalidomide components were passed through a #30 mesh screen (about 430μ to about 655μ). The Pluronic F-68® (manufactured by JRH Biosciences, Inc. of Lenexa, Kans.) surfactant was passed through a #20 mesh screen (about 457μ to about 1041μ). The Pluronic F-68® surfactant and 0.5 kgs of croscarmellose sodium were loaded into a 16 qt. twin shell tumble blender and mixed for about 5 minutes. The mix was then transferred to a 3 cubic foot twin shell tumble blender where the microcrystalline cellulose was added and blended for about 5 minutes. The thalidomide as added and blended for an additional 25 minutes. This pre-blend was passed through a roller compactor with a hammer mill attached at the discharge of the roller compactor and moved back to the tumble blender. The remaining croscarmellose sodium and magnesium stearate was added to the tumble blender and blended for about 3 minutes. The final mixture was compressed on a rotary tablet press with 250 mg per tablet (200,000 tablet batch size).

5.3. Example 3

Prior Art Thalidomide Dosage Unit

Table 4 illustrates a prior art batch formulation and a single dose unit formulation for a 50 mg, i.e., 12.5 percent by weight, thalidomide single dose unit sized to a capsule of size #0.

TABLE 4

Formulation for 50 mg Thalidomide single dosage unit of size #0

| Material | Percent by Weight | Quantity (mg/tablet) | Quantity (kg/batch) |
|---|---|---|---|
| Thalidomide | 12.5% | 50.0 | 7.50 |
| Microcrystalline Cellulose | 15.0% | 60.0 | 9.00 |
| Kollidon 90F USP[1] | 3.0% | 12.0 | 1.80 |
| Stearic Acid NF | 1.0% | 4.0 | 0.60 |
| Colloidal Silicon Dioxide | 0.2% | 0.8 | 0.12 |
| Crospovidone NF | 4.0% | 16.0 | 2.40 |
| Anhydrous lactose NF | 64.3% | 257.3 | 38.58 |
| Total | 100.0% | 400.0 mg | 60.00 kg |

[1]Also manufactured as Povidone 90F USP by BASF

Microcrystalline cellulose, KOLLIDON 90F, stearic acid, colloidal silicon dioxide, crospovidone, and anhydrous lactose were individually weighed and passed through a 710 μ screen. The raw materials were transferred into a bowl or Fielder blender. Subsequently, the quantity of milled thalidomide was weighed and added to the raw materials through the screen, followed by adding the anhydrous lactose. The mixture was blended for about 2.5 minutes to about 6 minutes, until the mixture was homogenous. The blend was compressed by passing the blend through a roller compactor (Alexanderwerk Compactor WP 50 N/75). Thereafter, the mixture was encapsulated using a Zanasi AZ20 encapsulating machine (150,000 capsule batch size). The blend mixture was loaded into size #0 hard gelatin capsules to the desired fill weight of powder and 50 mg of thalidomide.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A single unit dosage form in the form of a size 4 capsule comprising a uniform admixture of 50 mg thalidomide and 74 mg of pregelatinized corn starch.

2. The dosage form of claim 1, which further comprises magnesium stearate.

3. The dosage form of claim 2, wherein the magnesium stearate is present in an amount of 1 mg.

4. The dosage form of claim 3, the contents of which weighs 125 mg.

5. A single unit dosage form in the form of a size 2 capsule, the contents of which weighs 250 mg, and comprising 100 mg of thalidomide and pregelatinized corn starch.

6. The dosage form of claim 5, which further comprises magnesium stearate.

7. A single unit dosage form in the form of a size 0 capsule comprising a uniform admixture of 200 mg of thalidomide and 297.5 mg of pregelatinized corn starch.

8. The dosage form of claim 7, which further comprises magnesium stearate.

9. The dosage form of claim 8, wherein the magnesium stearate is present in an amount of 2.5 mg.

10. The dosage form of claim 9, the contents of which weighs 500 mg.

* * * * *